(12) United States Patent
Takino et al.

(10) Patent No.: US 7,207,978 B2
(45) Date of Patent: Apr. 24, 2007

(54) PULL-ON DISPOSABLE DIAPER

(75) Inventors: Shunsuke Takino, Kagawa-ken (JP); Toshifumi Otsubo, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 0 days.

(21) Appl. No.: 10/945,989

(22) Filed: Sep. 22, 2004

(65) Prior Publication Data

US 2005/0038404 A1 Feb. 17, 2005

Related U.S. Application Data

(63) Continuation of application No. PCT/JP03/03017, filed on Mar. 13, 2003.

(30) Foreign Application Priority Data

Mar. 25, 2002 (JP) ............................. 2002-083560

(51) Int. Cl.
*A61F 13/15* (2006.01)

(52) U.S. Cl. .................. 604/385.201; 604/385.27; 604/385.28

(58) Field of Classification Search ........... 604/385.01, 604/385.201, 385.25–385.28, 393–396, 400
See application file for complete search history.

(56) References Cited

U.S. PATENT DOCUMENTS

| | | | | |
|---|---|---|---|---|
| 3,744,494 A | * | 7/1973 | Marsan | 604/378 |
| 3,774,610 A | * | 11/1973 | Eckert et al. | 604/365 |
| 3,968,799 A | * | 7/1976 | Schrading | 604/365 |
| 4,636,207 A | * | 1/1987 | Buell | 604/370 |
| 6,440,117 B1 | * | 8/2002 | Itoh et al. | 604/385.28 |
| 6,666,851 B2 | * | 12/2003 | Otsubo et al. | 604/385.201 |

FOREIGN PATENT DOCUMENTS

| | | |
|---|---|---|
| JP | 47-36734 | 12/1972 |
| JP | 50-21845 | 3/1975 |
| JP | 50-33044 | 3/1975 |
| JP | 2002-035033 | 2/2002 |
| JP | 2003-10244 | 1/2003 |

* cited by examiner

*Primary Examiner*—Tatyana Zalukaeva
*Assistant Examiner*—C. Lynne Anderson
(74) *Attorney, Agent, or Firm*—Lowe Hauptman & Berner LLP (57) ABSTRACT

A pull-on disposable diaper has front and rear waist covering regions and a crotch covering region wherein a bodily discharge absorbing component extends over the crotch covering region into the front and rear waist covering regions. In the crotch covering region, the bodily discharge absorbing component is folded inward along first, second and third folding guides in a transverse direction of the absorbing component. A pair of flaps are formed along transversely opposite lateral side edges of the bodily discharge absorbing component. In each of the flaps, a first lateral marginal edge extending along the associated lateral edge is bonded to an outer surface of the bodily discharge absorbing component and a second lateral marginal edge lies on the side of an inner surface of the absorbing component. An elastic member is attached to the flap in a stretched state in a longitudinal direction of the flap.

3 Claims, 9 Drawing Sheets

PULL-ON DISPOSABLE DIAPER

TECHNICAL FIELD OF THE INVENTION

This invention relates to a pull-on disposable diaper for absorption and containment of bodily discharges.

BACKGROUND ART OF THE INVENTION

Figure 10:
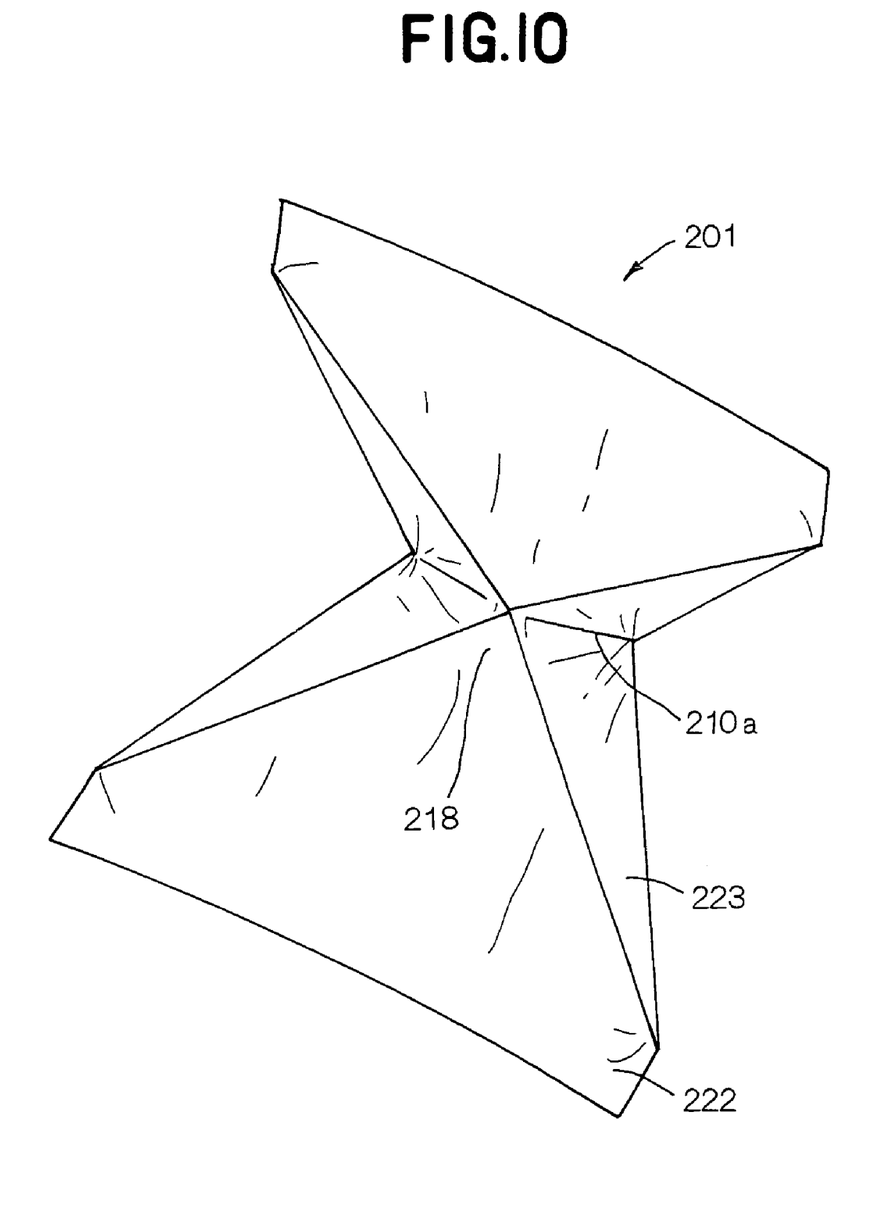
FIG. 10 is a perspective view showing a conventional diaper.

Japanese Patent Application No. 1975-33044A discloses a foldup-type disposable diaper 201 as shown in FIG. 10 of the accompanying drawings. This diaper 201 is composed of a liquid-absorbent pad, a liquid-pervious inner sheet 222 and a liquid-impervious outer sheet 223 so as to present a rectangle and this rectangle is then folded along a transversal 210*a* orthogonal to long sides of the rectangle in two halves in a longitudinal direction. Simultaneously, the rectangle is tucked from its transversely opposite edges inwardly of the diaper, more specifically, toward a middle point of the transversal 210*a* so as to form pockets 218. This diaper is adapted to be worn in combination with use of a diaper cover and surface sections of the sheet 223 facing each other as the rectangle is tucked inward in this manner are partially bonded to each other in order to prevent the respective pockets 218 might get out of initial shapes thereof even after the diaper has been developed to put the diaper on a wearer's body. The diaper arranged in such a manner is effective to avoid leakage of bodily discharges regardless of its rectangular shape because a region of the diaper intended to cover the wearer's crotch is sufficiently narrow to be placed closely against the wearer's crotch.

Japanese Utility Model Application No. 1972-36734A discloses a foldup-type diaper made from a rectangular strip. This diaper also is adapted to be worn in combination with use of a diaper cover and the diaper is tucked inward from its transversely opposite edges in a longitudinally middle zone of the diaper. The crotch region of the diaper obtained in this manner has its width sufficiently reduced to be placed closely against the wearer's crotch and thereby to alleviate an anxiety of sideways urine leakage.

Both of the above-cited conventional diapers are of the rectangular open-type and adapted to be put on an infant's body by flatly developing the diaper and applying this to the hip of the infant lying on his or her back. However, it is likely that the regions of the diaper having previously been folded and tucked might get out of initial shapes thereof as the diaper is flattened and the function of these regions might be insufficient after the diaper has been put on the wearer's body. The diaper disclosed in Japanese Patent Application No. 1975-33044A intends to prevent the diaper from getting out of its initial shape by partially bonding together the surface sections opposed to each other as the diaper is folded and tucked. However, such bonding may obstruct the diaper to be flatly developed and retard operation of putting the diaper on the wearer's body. The diaper disclosed in the above-cited Japanese Utility Model Application No. 1972-36734A is accompanied with an inconvenience that the crotch region folded and tucked in this manner may get out of its desired shape as the diaper is flatly unfolded.

DISCLOSURE OF THE INVENTION

It is an object of this invention to provide a pull-on disposable diaper having a bodily discharge absorbing component folded in a crotch covering region improved so that the diaper can be quickly put on a wearer's body without the anxiety that the tucked bodily discharge absorbing component might get out of its desired shape.

In accordance with this invention, there is provided a pull-on disposable diaper having a height direction and a transverse direction being orthogonal to the height direction, the diaper being substantially symmetric about a center line bisecting a dimension of the diaper in the transverse direction, the diaper comprising a pants-like covering component having an inner surface and an outer surface opposed to the inner surface and a bodily discharge absorbent component, the covering component being composed of a front waist covering region, a rear waist covering region and a crotch covering region adapted to cover a wearer's front region, a wearer's rear region and a wearer's crotch region, respectively, so as to define a waist-hole and a pair of leg-holes, and the bodily discharge absorbing component lying on the inner surface and extending over the crotch covering region into the front and rear waist covering regions.

The pull-on disposable diaper further comprises the bodily discharge absorbing component including a liquid-absorbent core and a liquid-pervious cover sheet, the core being relatively long in a direction along which the bodily discharge absorbing component extends and having an inner surface and an outer surface opposed to the inner surface, the cover sheet covering at least the inner surface of the inner and outer surfaces of the core, the bodily discharge absorbing component being formed with a first folding guide extending from a middle zone between transversely opposite lateral edges which extend, in turn, parallel to each other in the height direction to respective the lateral edges in the front waist covering region, a second folding guide extending in the similar manner to respective the lateral edges in the rear waist covering region and a third folding guide extending in the transverse direction between the first and second folding guides, and the absorbing component being folded on both sides of the center line along the third folding guide so that the core has its outer surface sections facing to each other and along the first and second folding guides so that the core has its inner surface sections facing to each other; and the bodily discharge absorbing component formed along the lateral edges with flaps each having first and second lateral marginal edges extending parallel to the lateral edges of the bodily discharge absorbing component and first and second ends extending in a direction intersecting the lateral edges of the bodily discharge absorbing component, the first and second lateral marginal edges being folded around the associated lateral edge of the bodily discharge absorbing component so as to lie on the side of an outer surface and on the side of an inner surface of the bodily discharge absorbing component, respectively, the first and second ends respectively joined to front and rear ends of the bodily discharge absorbing component lying in the front and rear waist covering regions, respectively, and the second lateral marginal edge provided with elastic members attached thereto in a stretched state in a longitudinal direction of the flap.

This invention includes the following embodiments.

Each of the flaps is provided in its intermediate zone defined between the first and second lateral marginal edges with a second elastic members attached thereto in a stretched state in the longitudinal direction of this flap.

The second elastic members are attached to the flap on its zone opposed to the outer surface of the bodily discharge absorbing component.

In the crotch covering region, the cover sheet is folded back along the lateral edges so as to cover the inner surface as well as the outer surface of the core and, in a vicinity of the lateral edges, the core is able to absorb the bodily discharges from the inner as well as from the outer surfaces through the cover sheet.

DESCRIPTION OF THE BEST MODE FOR WORKING OF THE INVENTION

Details a pull-on disposable diaper according to this invention will be more fully understood from the description given hereunder with reference to the accompanying drawings.

Figure 1:
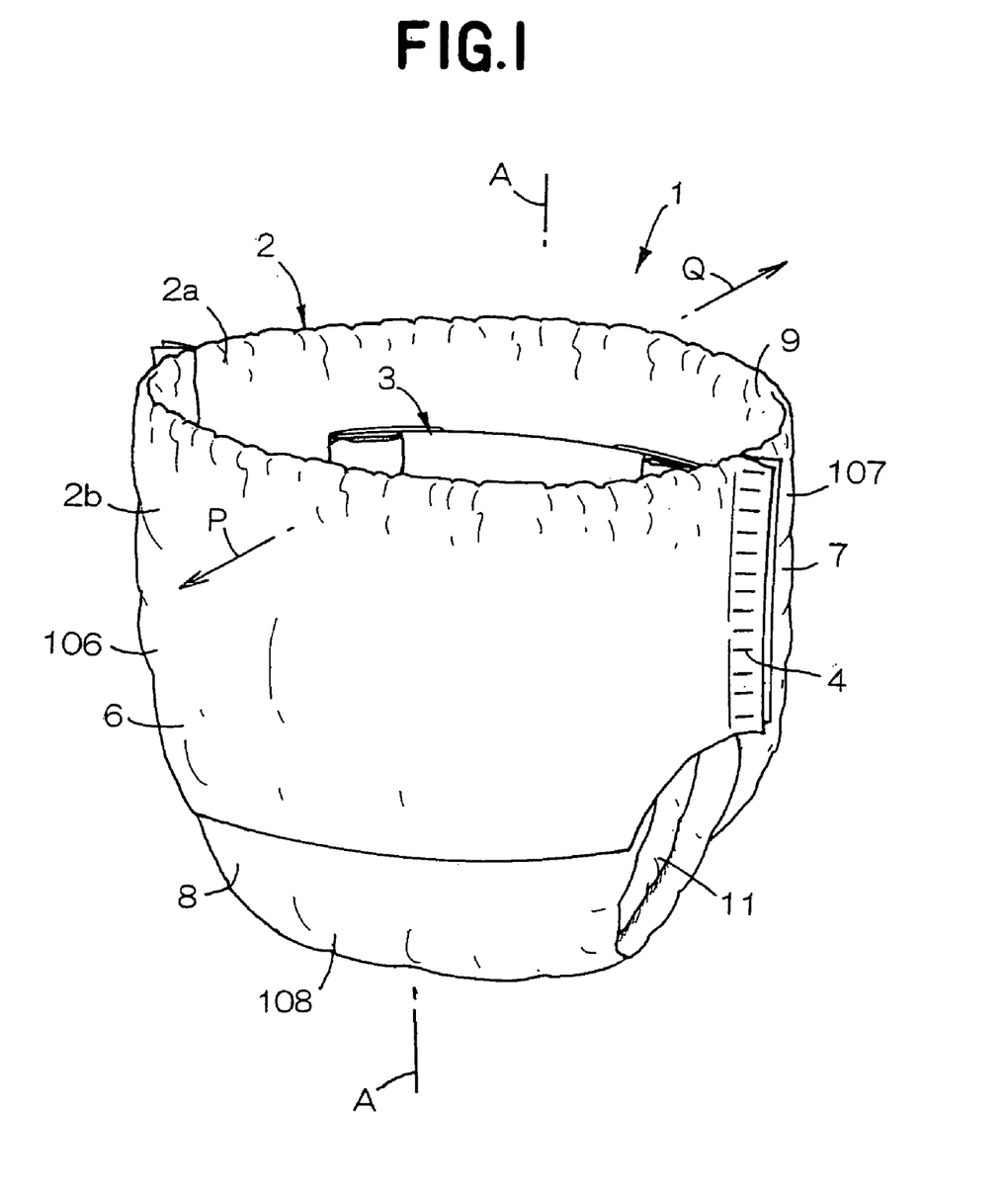
FIG. 1 is a perspective view showing a pull-on disposable diaper.
Figure 2:
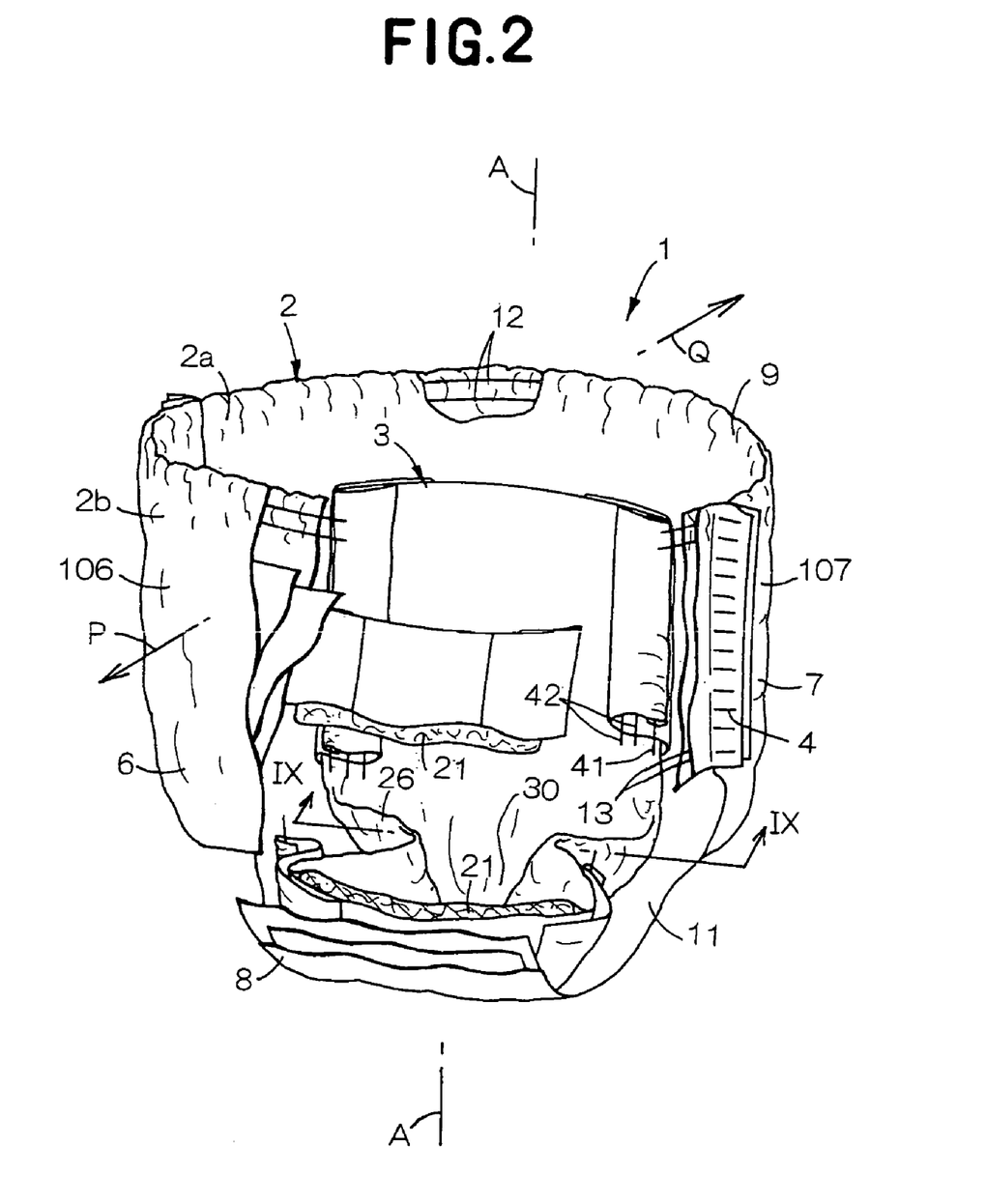
FIG. 2 is a partially cutaway perspective view showing the diaper of FIG. 1.

FIG. 1 is a perspective view showing a pull-on disposable diaper 1 and FIG. 2 is a partially cut away perspective view showing this diaper 1. The diaper 1 has a height direction corresponding to a vertical direction in FIGS. 1 and 2 and a transverse direction orthogonal to the height direction. The diaper 1 basically comprises a pants-like covering component 2 and a bodily discharge absorbing component 3. The transverse direction is also a width direction of the diaper 1. The covering component 2 has an inner surface 2a facing a wearer's body and an outer surface 2b facing a wearer's garment. This covering component 2 is composed of a front waist covering region 6, a rear waist covering region 7 and a crotch covering region 8 adapted to cover a wearer's front, rear and crotch regions, respectively. The front and rear waist covering regions 6, 7 are overlaid and joined together along transversely opposite lateral marginal edges at a plurality of zones 4 arranged intermittently in a vertical direction along the opposite lateral marginal edges so that the front waist covering region 6, the rear waist covering region 7 and the crotch covering region 8 cooperate one with another to define a waist-hole 9 and a pair of leg-holes 11. The waist-hole 9 is provided along its peripheral marginal edge with a plurality of waist elastic members 12 attached in a stretched state thereto. For the leg-holes 11, a pair of sheets 106, 107 forming the front and rear waist covering regions 6, 7 and defining approximate upper half peripheral edges of the respective leg-holes 11 are respectively provided along these peripheral edges thereof with a plurality of leg elastic members 13 attached in a stretched state thereto so as to describe substantially circular arcs (See FIG. 8 also). The bodily discharge absorbing component 3 is disposed on the inner surface 2a of the covering component 2 and extends over the crotch covering region 8 into the front and rear waist covering regions 6, 7. The bodily discharge absorbing component 3 is folded toward a longitudinal center line A—A (See FIG. 3) bisecting a width of the diaper 1, i.e., inward in a transverse direction of the diaper 1.

Figure 3:
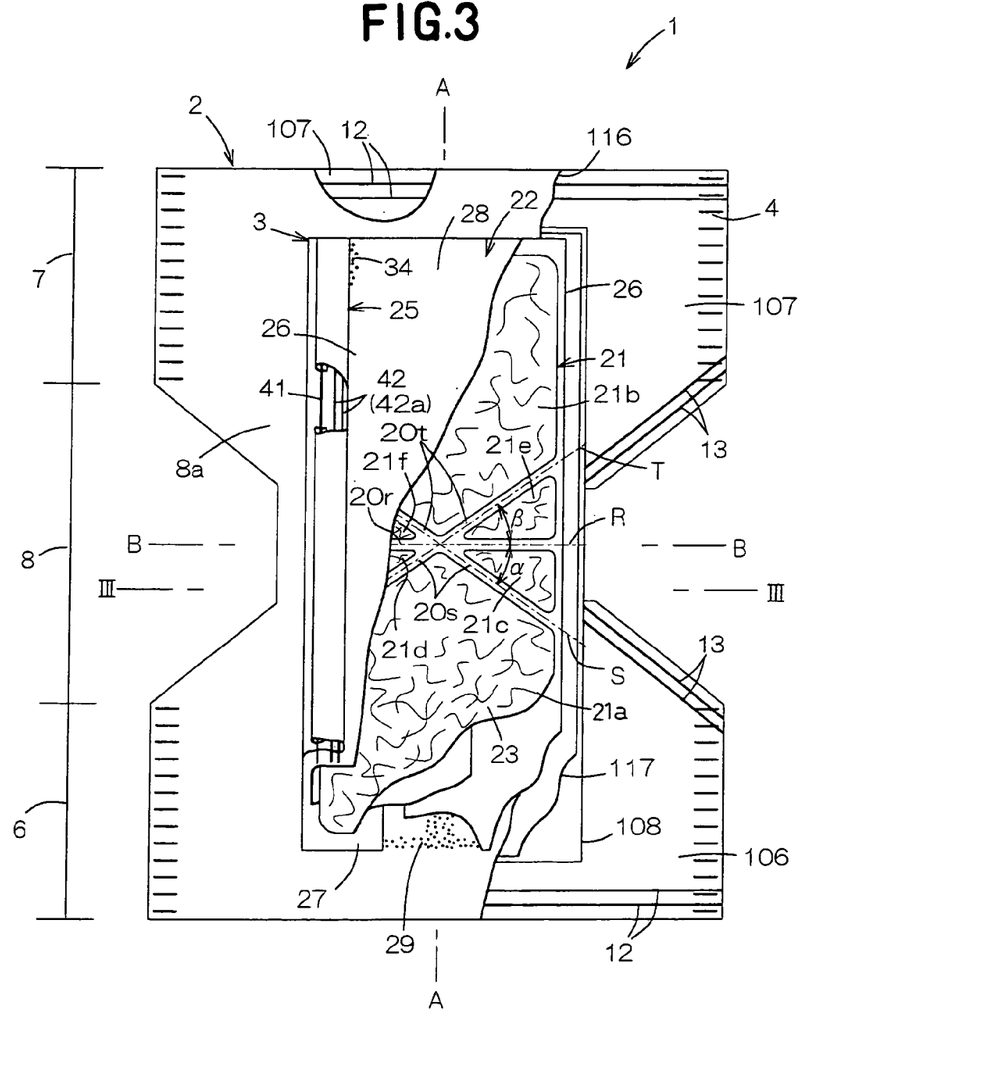
FIG. 3 is a developed plan view showing the diaper of FIG. 1.
Figure 4:
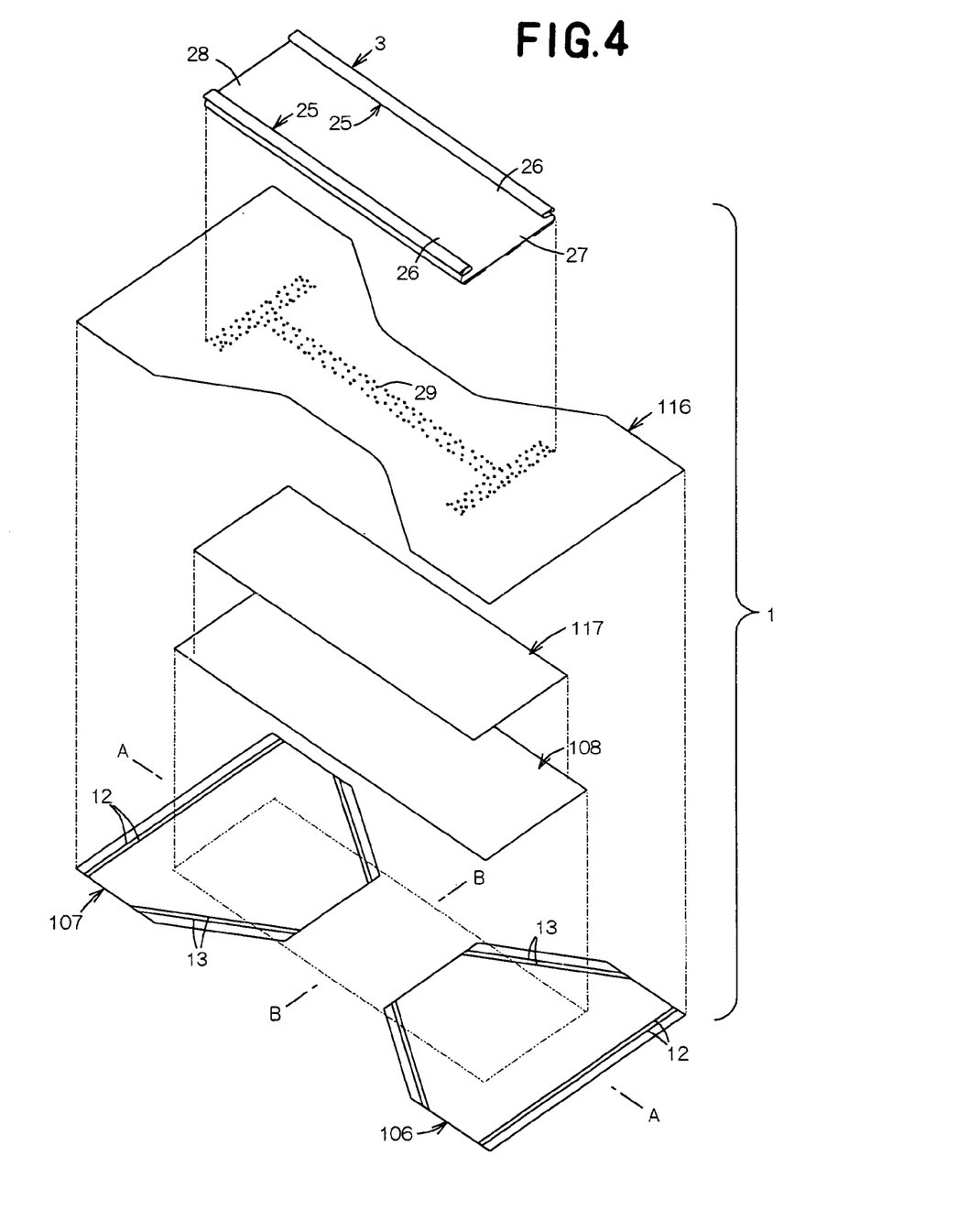
FIG. 4 is an exploded perspective view showing the diaper of FIG. 3.

FIG. 3 is a partially cutaway plan view showing the diaper 1 of FIG. 1 with front and rear waist regions 6, 7 as having been separated from each other at joining zones 4 and developed in directions indicated by arrows P, Q, respectively, and FIG. 4 is an exploded perspective view showing the diaper 1 in such a developed state as seen in FIG. 3. As shown, the developed diaper 1 has its length as viewed in a vertical direction of FIG. 3 bisected by a transverse center line B—B extending transversely of the diaper 1 in orthogonal relationship with the longitudinal center line A—A. In the developed state as shown in FIG. 3, the diaper 1 is substantially symmetric about the longitudinal center line A—A and may be folded back along the transverse center line B—B and joined together at the zones 4 to obtain the diaper 1 in the state as shown in FIG. 1.

The covering component 2 comprises a hexagonal front sheet 106 defining the front waist covering region 6 and a part of the crotch covering region 8, a hexagonal rear sheet 107 defining the rear waist covering region 7 and a part of the crotch covering region 8, and a rectangular center sheet 108 defining a part of the crotch covering region 8. Longitudinally opposite ends of the center sheet 108 are joined to respective inner surfaces (i.e., upper surfaces as viewed in FIG. 4) of the front and rear sheets 106, 107 by means of hot melt adhesive agents (not shown) and thereby connect the front and rear sheets 106, 107 to each other. A rectangular liquid-impervious intermediate sheet 117 made of a plastic film is placed upon an inner surface of the center sheet 108 and an hour glass-shaped inner sheet 116 is placed upon an inner surface of the intermediate sheet 117. The intermediate sheet 117 is of a substantially same shape as the center sheet 108 but slightly smaller than the center sheet 108. The inner sheet 116 is the substantially same in size as well as in shape as the hourglass-configuration defined by the front sheet 106, the rear sheets 107 and the center sheet 108 connected together. These sheets 106, 107, 108, 117 and 116 are laminated one on another and intermittently joined together in overlaid area of these sheets. The rectangular bodily discharge absorbing component 3 is joined to the inner surface of the inner sheet 116 so that the longer sides of the rectangle defined by the bodily discharge absorbing component 3 may extend in the longitudinal direction of the center sheet 108. The absorbing component 3 has its longitudinally opposite ends 27, 28 and a transversely middle zone extending between these ends 27, 28 joined to the inner sheet 116 by means of a hot melt adhesive agent 29 applied on the inner sheet 116.

The absorbing component 3 has a rectangular shape which is relatively long in a vertical direction as viewed in FIG. 3. This rectangular absorbent component 3 is contoured by transversely opposite lateral edges 26 extending in parallel to the longitudinal center line A—A and front and rear ends 27, 28 extending in the transverse direction (i.e., width direction) of the diaper 1 in orthogonal relationship with the transversely opposite lateral edges 26. Along the lateral edges 26, there are provided a pair of flaps 25, respectively. The absorbing component 3 comprises a core 21 and a cover sheet 22 joined to the inner surface 2a of the covering component 2 by means of the hot melt adhesive agent 29. The core 21 is formed by absorbent materials such as fluff pulp or super-absorbent polymer particles compressed under appropriate pressure. While the core 21 is illustrated to define a rectangle in entirety, it should be understood that the core 21 has grooves 20r, 20s, 20t extending along a chain line R extending in coincidence with the transverse center line B—B, a chain line S extending so as to describe a V-shape from a central zone of the core 21 defined by the intersection of the longitudinal center line A—A and the transverse center line B—B toward the front waist covering region 6 to the transversely opposite lateral edges 26 and a chain line T extending so as to describe a V-shape from the central zone of the core 21 defined by the intersection of the longitudinal center line A—A and the transverse center line B—B toward the rear waist covering region 7 to the transversely opposite lateral edges 26. These grooves 20r, 20s, 20t divide the core 21 into core elements 21a, 21b, 21c, 21d, 21e, 21f.

Figure 5:
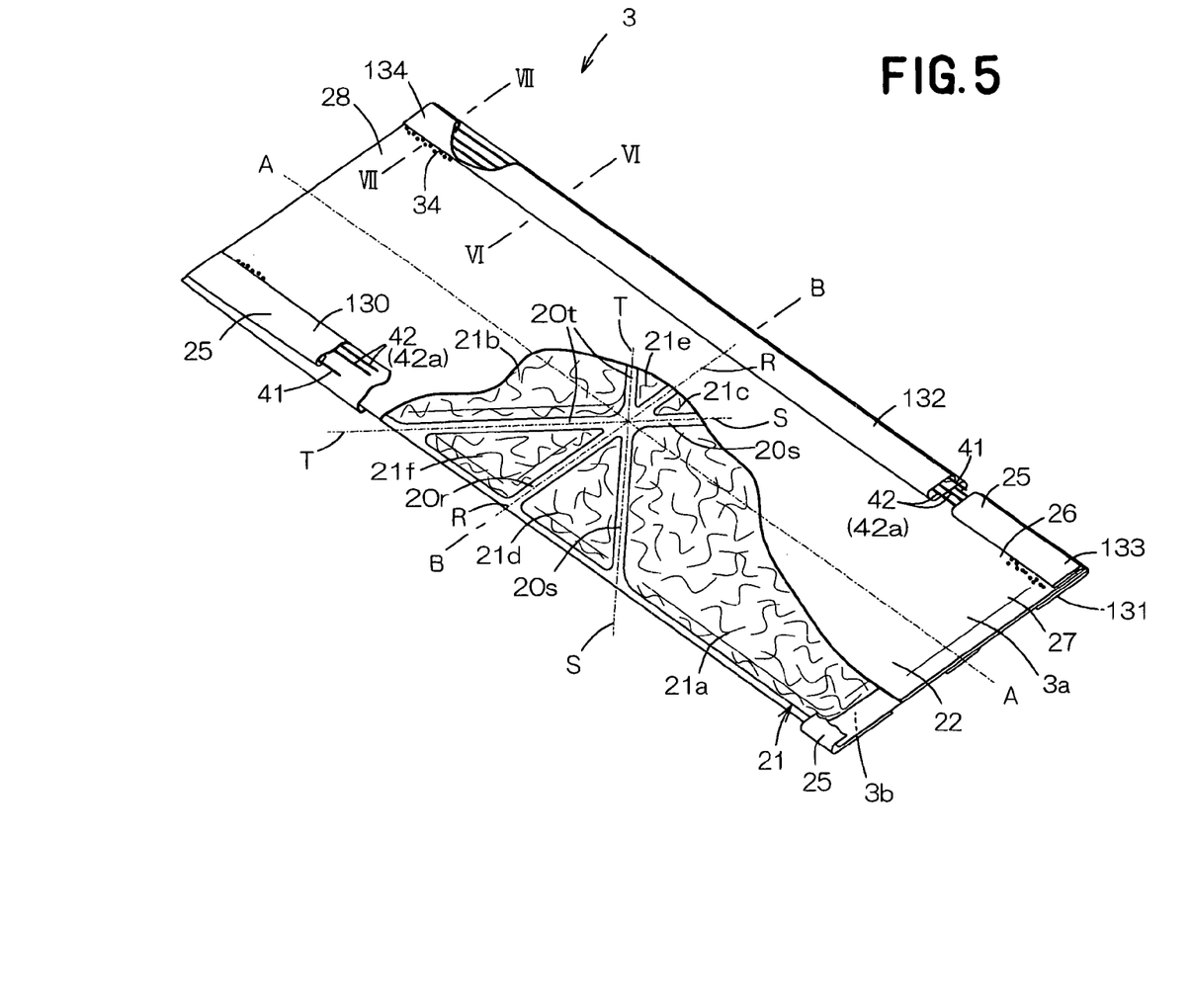
FIG. 5 is a partially cutaway perspective view showing an absorbing component.
Figure 6:
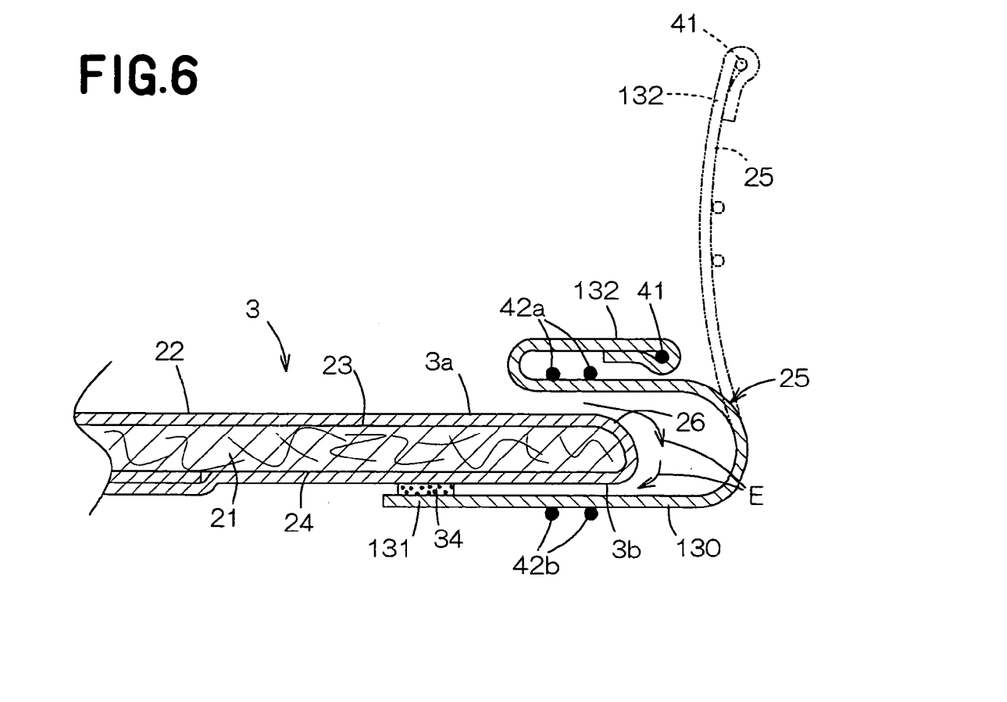
FIG. 6 is a sectional view taken along a line VI—VI in FIG. 5.
Figure 7:
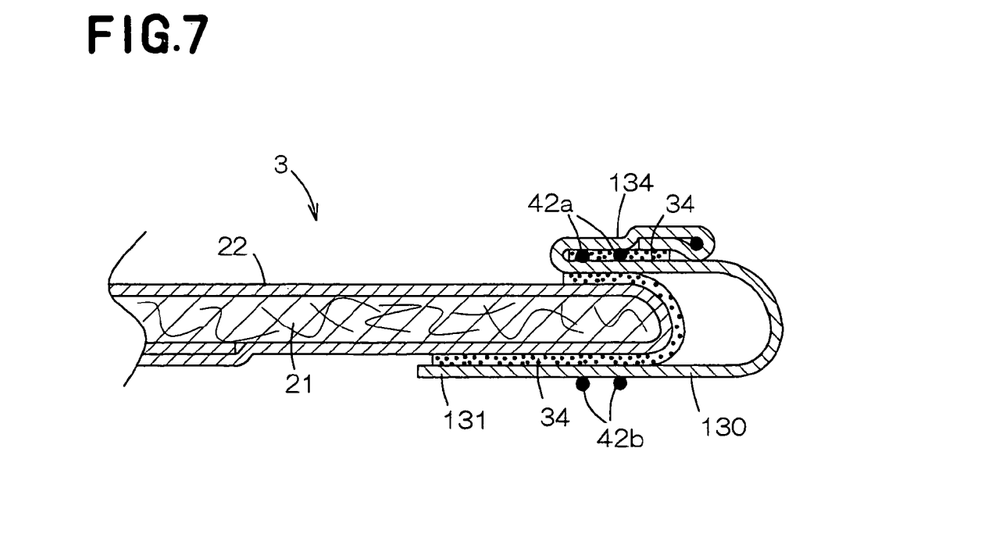
FIG. 7 is a sectional view taken along a line VII—VII in FIG. 5.

FIG. 5 is a partially cutaway perspective view showing the absorbing component 3 and FIGS. 6 and 7 are sectional views taken along lines VI—VI and VII—VII, respectively, in FIG. 5. The flaps 25 are formed by leak-barrier sheets 130 respectively extending along the lateral edges 26 of the absorbing component 3. The leak-barrier sheet 130 is made of a hydrophobic, preferably liquid-impervious, more preferably breathable liquid-impervious nonwoven fabric or a plastic film and folded in the transverse direction of the diaper 1 so as to present a Z- or inverted Z-shaped cross-section. The flap 25 has a first lateral marginal edge 131 lying on the side of an outer surface 3b of the absorbing component 3 and a second lateral marginal edge 132 lying on the side of an inner surface 3a of the absorbing component 3. The first lateral marginal edge 131 is secured to the cover sheet 22 by means of an adhesive agent 34. The second lateral marginal edge 132 lies above the inner surface 3a and deformable in a vertical direction as well as in a horizontal direction as viewed in FIGS. 6 and 7. The outermost marginal edge of the second lateral marginal edge 132 is folded back so as to wrap a first elastic member 41 attached in a stretched state to this outermost marginal edge. Between the first and second lateral marginal edges 131, 132, the leak-barrier sheet 130 extends from the first lateral marginal edge 131 toward the second lateral marginal edge 132 beyond the associated lateral edge 26 of the absorbing component 3, then the sheet 130 is folded back toward the inner surface 3a and folded back again outwardly beyond the associated lateral edge 26 of the absorbing component 3. It should be noted that, at the longitudinally opposite ends 27, 28 of the absorbing component 3, first and second ends 133, 134 of the flap 25 formed by the leak-barrier sheet 130 folded in a Z- or inverted Z-shape are held in such a folded state by means of the adhesive agent 34. More specifically, not only the respective layers of the leak-barrier sheet 130 folded in a Z- or inverted Z-shape to form the flap 25 but also the cover sheet 22 and the leak-barrier sheet 130 are joined together, by means of the adhesive agent 34. The first elastic member 41 has its longitudinally opposite ends fixed to the longitudinally opposite ends 27, 28 of the absorbing component 3, respectively, by means of the leak-barrier sheet 130. In addition to the first elastic member 41, the flap 25 may be provided in an intermediate zone between the first and second lateral marginal edges 131, 132 with elastic member 42 extending in the longitudinal direction and attached in a stretched state to this intermediate zone. The second elastic member 42 extends in parallel to the first elastic member 41 and is provided between the first and second ends 133, 134 at least in the crotch covering region 8. As shown in FIG. 6, the second elastic member 42 may comprise elastic members (42a) attached to the flap 25 so as to lie above the inner surface 3a of the absorbing component 3 and/or elastic members (42b) attached to the flap 25 so as to lie below the outer surface 3b of the absorbing component 3.

The sheets 106, 107, 108, 117, 116 and the absorbing component which are laminated and bonded together in the successive steps illustrated by FIG. 4 may be folded back along the transverse center line B—B with the absorbing component 3 inside and then the front sheet 106, the rear sheet 107 and the inner sheet 116 may be joined together along the respective lateral edges thereof at the bonding zones 4 shown in FIG. 1 to obtain the diaper 1 in the state as shown in FIGS. 1. Thereupon, both side portions of the absorbing component 3 in the crotch covering region 8 with respect to the longitudinal center line A—A are folded as shown in FIG. 2. More specifically, the absorbing component 3 is folded along the groove 20r so that the outer surface 24 of the core element 21c is opposed to the outer surface 24 of the 21e (See FIG. 6) while the outer surface 24 of the core element 21d is opposed to the outer surface 24 of the core element 21f. At the same time, the absorbing component 3 is folded along the groove 20s and the groove 20t so that the inner surface 23 of the core element 21a (See FIG. 6) is opposed to the inner surfaces 23 of the respective core elements 21c, 21d while the inner surface 23 of the core element 21b is opposed to the inner surfaces 23 of the respective core elements 21e, 21f. In the absorbing component 3, the grooves 20r, 20s, 20t are free from the core 21 or contain the core 21 at an extremely low density, so the absorbing component 3 has its stiffness lower in these grooves 20r, 20s, 20t than in the other region. In addition, the portion of the absorbing component 3 lying along the longitudinal center line A—A are joined to the inner surface 2a of the covering component 2 but the opposite lateral edges 26 as well as the vicinity of these lateral edges 26 are not joined to the inner surface 2a of the covering component 2 as will be apparent from FIGS. 3 and 4. This arrangement facilitates the absorbing component 3 to be folded along the grooves 20r, 20s, 20t as shown in FIG. 1.

Figure 8:
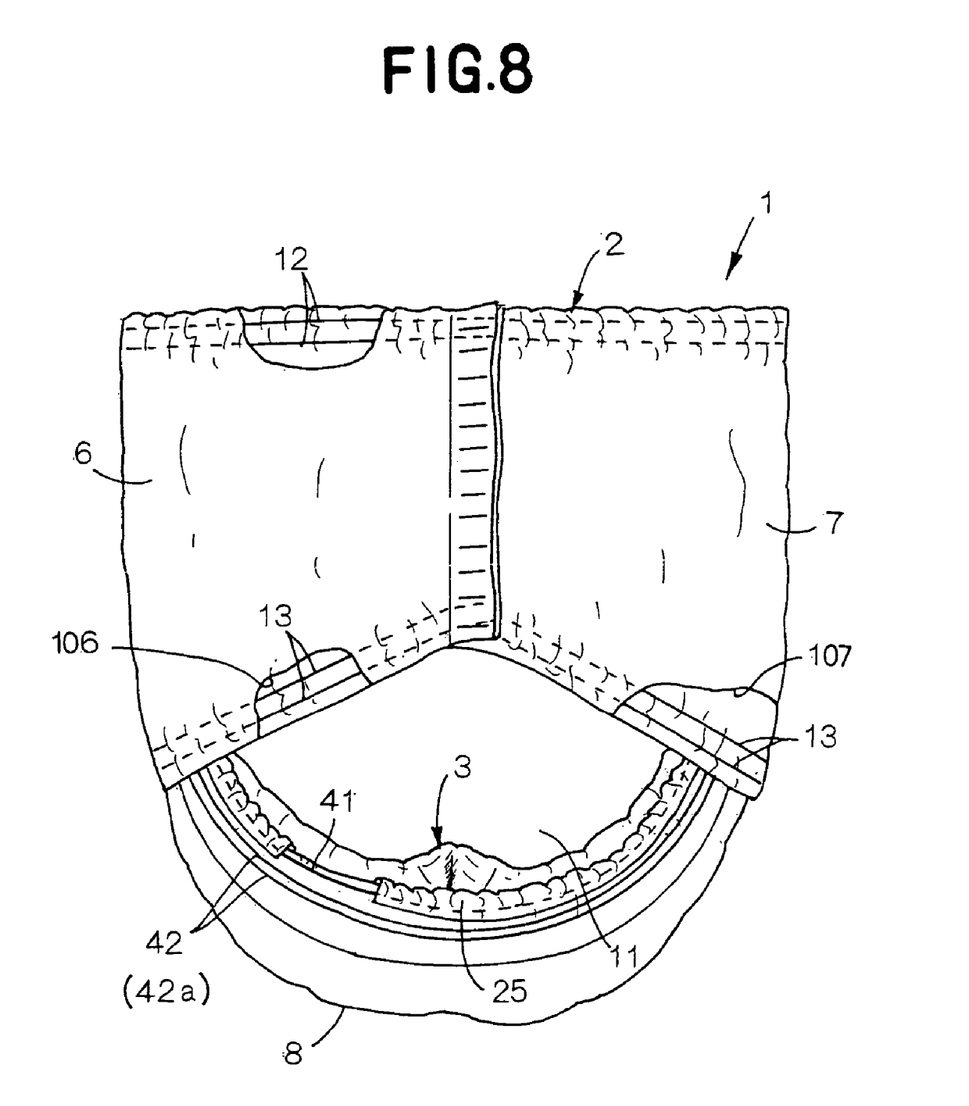
FIG. 8 is a partially cutaway side view showing the diaper of FIG. 1.
Figure 9:
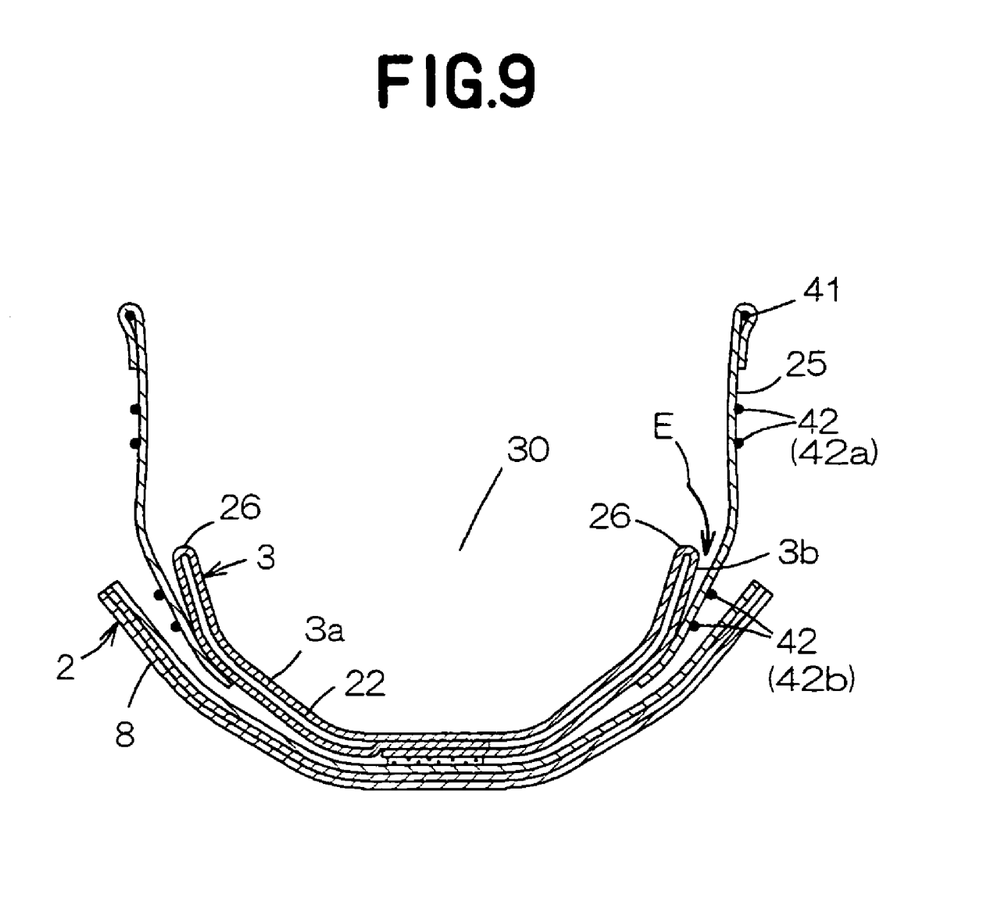
FIG. 9 is a sectional view taken along a line IX—IX in FIG. 2.

FIG. 8 is a partially cutaway side view showing the diaper 1 of FIG. 1 and FIG. 9 is a sectional view showing important parts along a line IX—IX in FIG. 2. In the sectional view shown in FIG. 8, the elastic members in a broken part are indicated by solid lines and the elastic members continuing into the solid lines are indicated by chain lines. The line IX—IX in FIG. 2 coincides with the transverse center line B—B extending inside the groove 20r in FIGS. 3 and 4. With the absorbing component 3 curving in the longitudinal direction as the diaper 1 is put on the wearer's body as shown in FIG. 1, the first elastic members 41 contract in the associated with the flap 25. In case that the flaps 25 has the second elastic members 42, the second elastic members 42 also contact at the same time. The portions of the flaps 25 defined between the longitudinally opposite ends 27, 28 of the absorbing component 3 rise above the inner surface 3a of the absorbing component 3 outside the lateral edges 26 thereof as the first and second elastic members 41, 42 contract. FIG. 9 shows the flaps 25 rising in this manner in the sectional view taken along the line IX—IX. The flap 25 indicated by an imaginary line in FIG. 6 rises in the vicinity of the end 28 of the absorbing component 3. The flaps 25 rising in this manner has the second lateral marginal edge 132 which can be tightly fit around the wearer's legs under stretching and contraction of the first and second elastic members 41, 42. The flaps 25 fitting around the wearer's legs in this manner prevent bodily discharges from sideways flowing beyond the lateral edges 26 of the absorbing component 3 and thereby prevent the bodily discharges from leaking out from the diaper 1. This preventive effect is particularly remarkable in the zone of the absorbing component 3 which has been folded in the crotch covering region 8 as seen in FIG. 2 so as to reduce the width of the component 3. Contraction of the first and second elastic members 41, 42 associated with these flaps 25 biases the absorbing component 3 to curve in the longitudinal direction in U-shape. Particularly the second elastic members 42 are arranged in the vicinity of the folded zones of the absorbing component 3 in the crotch covering region 8 and serve to hold these folded zones in initially folded states. Even when the folded zones of the absorbing component 3 are unfolded, the first and second elastic members 41, 42 biasing these zones to restore the initial folded states and prevent these zones from getting out of the respective initial folded states. In this way, the initial shapes of the folded zones in the absorbent component 3 are reliably held by the presence of the flaps 25 provided with the first and second elastic members 41, 42. In the flaps 25, the first elastic member 41 in the state shown in FIGS. 1 and 2 describes a U-shape and go substantially halves around the wearer's legs, respectively, and portions of the first elastic member 41 extending upward corresponding to the respective upper halves going halves around the wearer's legs indirectly overlap the leg elastic members 13 attached to the front and rear sheets 106, 107. These elastic members 13, 41 cooperate to ensure that the diaper 1 can fit around the entire circumferences of the respective legs. While the first elastic member 41 is illustrated to be the single elastic member, this may be replaced by a plurality of elastic members.

As will be apparent from FIGS. 6 and 9, the flap 25 is preferably constructed so as to be spaced downward from the outer surface 3b of the absorbing component 3 particularly in the vicinity of the lateral edge 26 of the component 3. With such an arrangement, a certain amount of bodily discharges flowing beyond the lateral edge 26 is able to flow in a direction indicated by an arrow E into a space defined between the outer surface 3b of the absorbing component 3 and the leak-barrier sheet 130 and to be absorbed by the core 21 from the outer surface 3b through the cover sheet 22.

In the pull-on disposable diaper 1 of FIG. 1 arranged as has been described, the opposite lateral edges 26, 26 of the absorbing component 3 folded so that the width of the absorbing component 3 may be reduced in the crotch covering region 8 advantageously come in close contact with the wearer's crotch. In addition, a space defined between these opposite lateral edges 26, 26 forms a pocket 30 (See FIGS. 2 and 9) serving to prevent a possibility that the inner surface of the absorbent component 3 wetted with absorbed urine might come in contact with the wearer's body over a large area and create an uncomfortable damp feeling against the wearer. Even if the bodily discharges flow beyond the lateral edges 26, the flaps 25 lying outside these lateral edges 26 function as barriers against leaking-out of the bodily discharges from the diaper 1. To put the diaper 1 on an infant's body, his or her mother may guide the infant's legs through the waist-hole 9 opened as widely as possible with the mother's hands put against the inner side of the waist-hole 9 into the respective leg-holes 11. With this diaper 1, the absorbing component 3 provided separately of the covering component 2 in the crotch covering region 8 remote from the waist-hole 9 is not affected by deformation of the diaper 1 occurring as the waist-hole 9 is opened in this manner. Furthermore, even if the absorbing component 3 gets out of its initial folded shape, contraction of the first and second elastic members 41, 42 for each of the flaps 25, particularly contraction of the second elastic member 42 which may be a plurality of elastic members extending in parallel one to another in the transverse direction of the flap 25 facilitates the absorbing component 3 to restore the initial folded state. With the absorbing component 3, the lateral edges of the folded region are reliably brought in close contact with the crotch of the infant. Therefore, the absorbing component 3 folded so as to reduce its width reliably provides its expected effect when the diaper 1 is put on the infant's body.

The pull-on disposable diaper according to this invention has advantageous effects that the bodily discharge absorbing component extending over the crotch region into the front and rear waist regions is folded so that the absorbing component may have its width reduced in the crotch region and be in contact with the wearer's body only along the transversely opposite side edges thereof. With this unique arrangement, the wearer is free from a damp feeling even after the bodily discharge absorbing component has absorbed bodily discharges. Combination of the bodily discharge absorbing component with the pants-like covering component ensures that the portion of the absorbing component folded so as to have its width reduced in the crotch region does not get out of the folded posture in the course of putting the diaper on the wearer's body. In addition, the elastic members attached to the flaps formed outside the lateral edges of the bodily discharge absorbing component normally bias the bodily discharge absorbing component to curve in the U-shape. Such a feature is effective to prevent the folded shape of the bodily discharge absorbing component from getting out of its desired shape and facilitates the operation of putting the diaper on the wearer's body in comparison with the conventional diaper.

What is claimed is:

1. A pull-on disposable diaper having a height direction and a transverse direction being orthogonal to said height direction, said diaper comprising:

a pants-type covering component having an inner surface and an outer surface opposed to said inner surface; and a bodily discharge absorbent component;

wherein said covering component comprises a front waist covering region, a rear waist covering region and a crotch covering region which define together a waist-hole and a pair of leg-holes;

said bodily discharge absorbing component is located on said inner surface of said covering component and extends over said crotch covering region into said front and rear waist covering regions; said bodily discharge absorbing component has transversely opposite lateral edges, which extend parallel to each other in said height direction, and a middle zone between said lateral edges; said bodily discharge absorbing component is formed with a first folding guide extending from the middle zone to respective said lateral edges in said front waist covering region, a second folding guide extending from said middle zone to respective said lateral edges in said rear waist covering region, and a third folding guide extending in said transverse direction between said first and second folding guides;

said bodily discharge absorbing component has a folded state in which said absorbing component is folded along said third folding guide so that an outer surface of said absorbing component has sections facing each other, and folded along said first and second folding guides so that an inner surface of said absorbing component has sections facing each other;

said diaper further comprises flaps formed along said lateral edges of said bodily discharge absorbing component, each said flap having first and second lateral marginal edges extending parallel to said lateral edges of said bodily discharge absorbing component and first and second ends; each said flap is folded around the associated lateral edge of said bodily discharge absorbing component so that said first and second lateral marginal edges of said flap lie on the side of the outer surface and on the side of the inner surface of said bodily discharge absorbing component, respectively;

said first and second ends of each said flap are respectively joined to front and rear ends of said bodily discharge absorbing component lying in said front and rear waist covering regions, respectively;

said diaper further comprises first elastic members each attached to said second lateral marginal edge of one of said flaps and contractible in a longitudinal direction of said flap;

the facing sections of the outer surface of said absorbing component are free of direct attachment to each other, and contraction of said first elastic members in the longitudinal direction maintains the bodily discharge absorbing component in the folded state;

the disposable diaper further comprises second elastic members each of which is attached to one of said flaps in an intermediate zone defined between said first and second lateral marginal edges of said flap and is contractible in said longitudinal direction of said flap;

the absorbing component includes, between the lateral edges, a middle portion and side portions on opposite sides of said middle portion;

the absorbing component is directly bonded to the inner surface of said covering component in said middle portion, and is not directly bonded to said covering component in said side portions and along said lateral edges; and contraction of said first and second elastic members raises at least said lateral edges of said absorbing component away from said covering component.

2. A pull-on disposable diaper, comprising:
a covering component having opposite inner and outer surfaces; and
a bodily discharge absorbent component;
wherein
said covering component comprises a front waist covering region, a rear waist covering region and a crotch covering region extending in a longitudinal direction of said diaper between said waist regions, transversely opposite side edges of the waist regions are permanently bonded to each other to define together a waist-hole and a pair of leg-holes;

said bodily discharge absorbing component is located on said inner surface of said covering component and extends over said crotch covering region into said front and rear waist covering regions;

said bodily discharge absorbing component has transversely opposite lateral edges and a middle zone between said lateral edges;

said bodily discharge absorbing component is formed with a first folding guide extending from the middle zone to respective said lateral edges in said front waist covering region, a second folding guide extending from said middle zone to respective said lateral edges in said rear waist covering region, and a third folding guide extending in a transverse direction of said diaper between said first and second folding guides;

said bodily discharge absorbing component has a folded state in which said absorbing component is folded along said third folding guide so that an outer surface of said absorbing component has sections facing each other, and folded along said first and second folding guides so that an inner surface of said absorbing component has sections facing each other;

said diaper further comprises flaps formed along said lateral edges of said bodily discharge absorbing component, each said flap having first and second lateral marginal edges extending in the longitudinal direction and first and second ends;

each said flap is folded around the associated lateral edge of said bodily discharge absorbing component so that said first and second lateral marginal edges of said flap lie on the side of the outer surface and on the side of the inner surface of said bodily discharge absorbing component, respectively;

said first and second ends of each said flap are respectively joined to front and rear ends of said bodily discharge absorbing component lying in said front and rear waist covering regions, respectively;

said diaper further comprises first elastic members each attached to the second lateral marginal edge of one of said flaps and contractible in said longitudinal direction;

each said flap has between the first and second ends thereof a middle portion which is not directly bonded to the absorbing component to define an opening to a pocket formed between said flap and the respective lateral edge of said absorbing component, thereby allowing bodily discharges to enter said pocket through said opening and to be absorbed by said absorbing component in a vicinity of said respective lateral edge of said absorbing component;

the disposable diaper further comprises second elastic members each of which is attached to one of said flaps in an intermediate zone defined between said first and second lateral marginal edges of said flap and is contractible in said longitudinal direction;

the absorbing component includes, between the lateral edges, a middle portion and side portions on opposite sides of said middle portion;

the absorbing component is directly bonded to the inner surface of said covering component in said middle portion, and is not directly bonded to said covering component in said side portions and along said lateral edges;

the first lateral marginal edge of each said flap is directly bonded to the outer surface of said absorbing component in one of said side portions; and contraction of said first and second elastic members raises said lateral edges and said side portions of said absorbing component away from said covering component.

3. The diaper of claim 2, wherein said flaps are free of direct attachment to the crotch covering region of said covering component.

* * * * *